United States Patent
Hoffmann et al.

(10) Patent No.: US 7,176,205 B2
(45) Date of Patent: Feb. 13, 2007

(54) BI-PYRIDINYL DERIVATIVES AS NK-1 ANTAGONISTS

(75) Inventors: Torsten Hoffmann, Weil am Rhein (DE); Patrick Schnider, Bottmingen (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 11/353,307

(22) Filed: Feb. 14, 2006

(65) Prior Publication Data

US 2006/0189626 A1   Aug. 24, 2006

(30) Foreign Application Priority Data

Feb. 22, 2005  (EP) .................................. 05101324

(51) Int. Cl.
*A61K 31/496* (2006.01)
*C07D 401/14* (2006.01)

(52) U.S. Cl. ........................... 514/253.01; 514/253.13; 544/364

(58) Field of Classification Search ................ 544/364; 514/253.01, 253.13
See application file for complete search history.

(56) References Cited

U.S. PATENT DOCUMENTS 5,972,938 A   10/1999   Rupniak et al.

FOREIGN PATENT DOCUMENTS

| EP | 1 035 115 | 9/2000 |
|----|-----------|--------|
| WO | WO 95/16679 | 6/1995 |
| WO | WO 95/18124 | 7/1995 |
| WO | WO 95/23798 | 9/1995 |
| WO | WO 05/002577 | 1/2005 |

OTHER PUBLICATIONS

Barker, R., Reviews in the Neuroscience, vol. 7, pp. 187-214, (1996).
Longmore et al., Can. J. Physiol. Pharmacol., vol. 75, pp. 612-621 (1997).
Kramer et al., Science, vol. 281, pp. 1640-1645, 1998.
Maggi et al., J. Auton. Pharmacol. vol. 13, pp. 23-93 (1993).
Navari et al., The New England Journal of Medicine, vol. 340, No. 3, pp. 190-195 (1999).

*Primary Examiner*—Emily Bernhardt
(74) *Attorney, Agent, or Firm*—George W. Johnston; Patricia S. Rocha-Tramaloni; Kimberly J. Prior

(57) ABSTRACT

The present invention relates to compounds of the formula

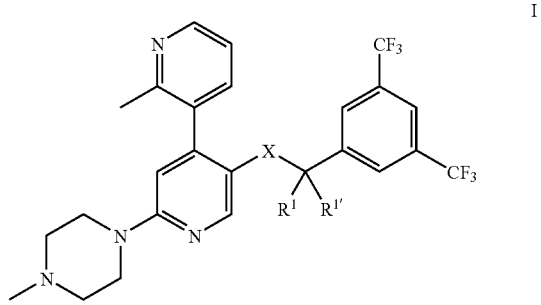

I wherein $R^1$ and $R^{1'}$ are each independently hydrogen or methyl and X is —C(O)N(CH$_3$)— or —N(CH$_3$)C(O)—, and to pharmaceutically acceptable acid addition salts thereof for the treatment of numerous inflammatory conditions, migraine, rheumatoid arthritis, asthma, inflammatory bowel disease, mediation of the emetic reflex, Parkinson's disease, anxiety, depression, psychosis, motion sickness, induced vomiting, pain, headache, migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, traumatic brain injury, motion sickness, emesis and psychoimmunologic and psychosomatic disorders.

7 Claims, No Drawings

BI-PYRIDINYL DERIVATIVES AS NK-1 ANTAGONISTS

PRIORITY TO RELATED APPLICATIONS

This application claims the benefit of European Application No. 05101324.1, filed Feb. 22, 2005, which is hereby incorporated by reference in its entirety.

BACKGROUND OF THE INVENTION

Substance P is a naturally occurring undecapeptide belonging to the tachykinin family of peptides, the latter being so-named because of their prompt contractile action on extravascular smooth muscle tissue. The receptor for substance P is a member of the superfamily of G protein-coupled receptors.

The neuropeptide receptor for substance P (NK-1) is widely distributed throughout the mammalian nervous system (especially brain and spinal ganglia), the circulatory system and peripheral tissues (especially the duodenum and jejunum) and are involved in regulating a number of diverse biological processes.

The central and peripheral actions of the mammalian tachykinin substance P have been associated with numerous inflammatory conditions including migraine, rheumatoid arthritis, asthma, and inflammatory bowel disease as well as mediation of the emetic reflex and the modulation of central nervous system (CNS) disorders such as Parkinson's disease (Neurosci. Res., 1996, 7, 187–214), anxiety (Can. J. Phys., 1997, 75, 612–621) and depression (Science, 1998, 281, 1640–1645).

Evidence for the usefulness of tachykinin receptor antagonists in pain, headache, especially migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases has been shown in "Tachykinin Receptor and Tachykinin Receptor Antagonists", J. Auton. Pharmacol., 13, 23–93, 1993.

Furthermore, Neurokinin 1 receptor antagonists are being developed for the treatment of a number of physiological disorders associated with an excess or imbalance of tachykinin, in particular substance P. Examples of conditions in which substance P has been implicated include disorders of the central nervous system such as anxiety, depression and psychosis (WO 95/16679, WO 95/18124 and WO 95/23798).

The neurokinin-1 receptor antagonists are further useful for the treatment of motion sickness and for treatment induced vomiting.

In addition, in The New England Journal of Medicine, Vol. 340, No. 3 190–195, 1999 has been described the reduction of cisplatin-induced emesis by a selective neurokinin-1-receptor antagonist.

Furthermore, U.S. Pat. No. 5,972,938 describes a method for treating a psychoimmunologic or a psychosomatic disorder by administration of a tachykinin receptor, such as NK-1 receptor antagonist.

SUMMARY OF THE INVENTION

The present invention provides compounds of formula I

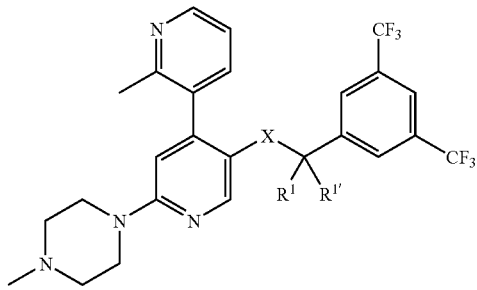

I wherein
$R^1$ and $R^{1'}$ are each independently hydrogen or methyl;
X is —C(O)N(CH$_3$)— or —N(CH$_3$)C(O)—;
and pharmaceutically acceptable acid addition salts thereof.

The following novel compounds of formula I are encompassed by the present invention:
2-methyl-6'-(4-methyl-piperazin-1-yl)-[3,4']bipyridinyl-3'-carboxylic acid (3,5-bis-trifluoromethyl-benzyl)-methyl-amide and
2-(3,5-bis-trifluoromethyl-phenyl)-N-methyl-N-[2-methyl-6'-(4-methyl-piperazin-1-yl)-[3,4']bipyridinyl-3'-yl]-isobutyramide.

The compounds of formula I are generically encompassed by WO05/002577, wherein such compounds are useful for the treatment of schizophrenia. Furthermore, structurally similar NK-1 antagonists are described in EP 1035 115 A1 for the treatment of depression, anxiety and emesis. In the past, the use of such compounds as active ingredients in standard pharmaceutical doses in standard galenical compositions was not possible in view of their low solubility, for example as i.v. application for the treatment of certain CNS disorders.

The invention also provides pharmaceutical compositions containing compounds of the invention. The invention further provides processes for the preparation of compounds of the invention and for the manufacture of pharmaceutical compositions containing them.

The present compounds of formula I and their salts have valuable improved therapeutic properties. The compounds of the present invention are antagonists of the Neurokinin 1 (NK-1, substance P) receptor, and they have advantages over related compounds described in the prior art. The present NK-1 antagonists of formula I have a very good solubility when compared with similar compounds disclosed in the prior art. A good solubility is an important requirement for potential pharmaceutical drugs.

The invention also provides methods for the treatment of numerous inflammatory conditions, migraine, rheumatoid arthritis, asthma, inflammatory bowel disease, mediation of the emetic reflex, Parkinson's disease, anxiety, depression, pain, headache, migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, traumatic brain injury, motion sickness, induced vomiting and psychoimmunologic and psychosomatic disorders.

The most preferred indications in accordance with the present invention are disorders of the central nervous system, for example the treatment of certain depressive disorders or emesis by the administration of NK-1 receptor antagonists. A major depressive episode has been defined as being a period of at least two weeks during which, for most of the day and nearly every day, there is either depressed mood or the loss of interest or pleasure in all, or nearly all activities.

DETAILED DESCRIPTION OF THE INVENTION

As used herein, "solubility" refers to the maximum amount of one substance that can be dissolved in another substance at a given temperature and pressure. The proportion of substances in a solution depends on their limits of solution. The solubility is the ability of one substance to blend uniformly with another, e.g. solid in liquid. Solids vary from 0 to 100% in their degree of solubility in liquids, depending on the chemical structure of the substances; to the extent that they are soluble, they lose their crystalline form and become molecularly or ionically dispersed in the solvent to form a true solution.

"Pharmaceutically acceptable," such as pharmaceutically acceptable carrier, excipient, etc., means pharmacologically acceptable and substantially non-toxic to the subject to which the particular compound is administered.

The term "pharmaceutically acceptable acid addition salts" embraces salts with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like.

"Therapeutically effective amount" means an amount that is effective to prevent, alleviate or ameliorate symptoms of disease or prolong the survival of the subject being treated.

The present invention provides compounds of formula I

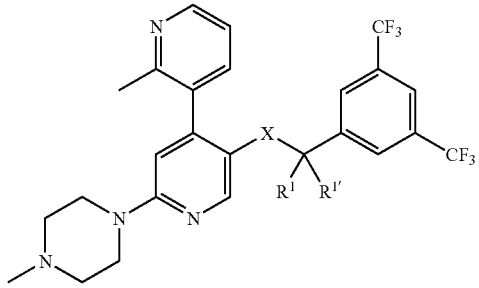

wherein
$R^1$ and $R^{1'}$ are each independently hydrogen or methyl;
X is —C(O)N(CH$_3$)— or —N(CH$_3$)C(O)—;
and pharmaceutically acceptable acid addition salts thereof.

In one aspect, the invention provides compounds of formula I in which $R^1$ and $R^{1'}$ are both hydrogen. In an other aspect, the invention provides compounds of formula I in which $R^1$ and $R^{1'}$ are both methyl.

In one aspect, the present invention provides compounds in which X is —C(O)N(CH$_3$).

In another aspect, the present invention provides compounds in which X is —N(CH$_3$)C(O)—.

The following novel compounds of formula I are encompassed by the present invention:
2-methyl-6'-(4-methyl-piperazin-1-yl)-[3,4']bipyridinyl-3'-carboxylic acid (3,5-bis-trifluoromethyl-benzyl)-methyl-amide and 2-(3,5-bis-trifluoromethyl-phenyl)-N-methyl-N-[2-methyl-6'-(4-methyl-piperazin-1-yl)-[3,4']bipyridinyl-3'-yl]-isobutyramide.

The present compounds of formula I and their pharmaceutically acceptable salts can be prepared by methods known in the art, for example, by processes described below, which processes comprise
a) reacting a compound of formula

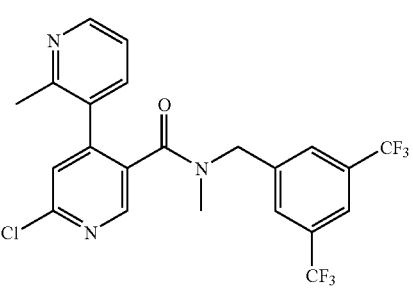

with 1-methyl-piperazine of formula

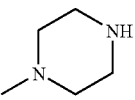

to give a compound of formula

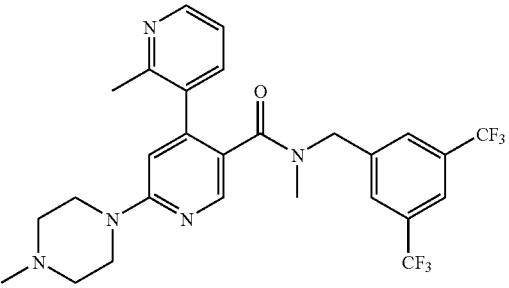

or
b) reacting a compound of formula

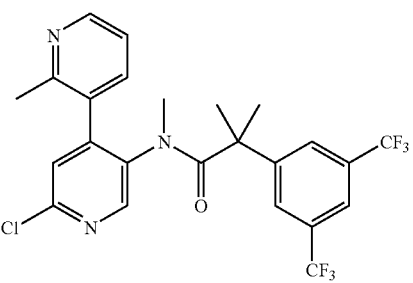

with 1-methyl-piperazine of formula

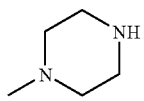

to give a compound of formula

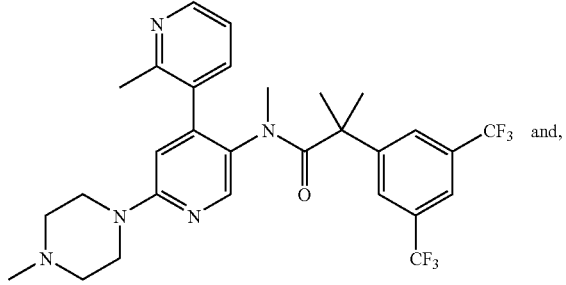

if desired, converting the compound obtained into a pharmaceutically acceptable acid addition salt.

In accordance with process variant a) a mixture of 6'-chloro-2-methyl-[3,4']bipyridinyl-3'-carboxylic acid (3,5-bis-trifluoromethyl-benzyl)-methyl-amide and 1-methylpiperazine is heated at about 120° C. for 2 h. After cooling to room temperature, the mixture is diluted with dichloromethane and washed with water. The aqueous layer is worked up in conventional manner to give the compound 2-methyl-6'-(4-methyl-piperazin-1-yl)-[3,4']bipyridinyl-3'-carboxylic acid (3,5-bis-trifluoromethyl-benzyl)-methyl-amide of formula I-1.

Process variant b) describes the reaction of a compound of formula II-2 with 1-methylpiperazine to produce a compound of formula I-2. A mixture of 2-(3,5-bis-trifluoromethyl-phenyl)-N-(6'-chloro-2-methyl-[3,4']bipyridinyl-3'-yl)-N-methyl-isobutyramide, 1-methylpiperazine and 4-(N,N-dimethylamino)pyridine is heated at about 140° C. overnight. After cooling to room temperature, the mixture is diluted with tert-butyl methyl ether and washed with water. The aqueous layer is extracted with tert-butyl methyl ether. The combined organic layers are dried and concentrated to give the compound 2-(3,5-bis-trifluoromethyl-phenyl)-N-methyl-N-[2-methyl-6'-(4-methyl-piperazin-1-yl)-[3,4']bipyridinyl-3'-yl]-isobutyramide of formula I-2.

The salt formation is effected at room temperature in accordance with methods which are known per se and which are familiar to any person skilled in the art. Not only salts with inorganic acids, but also salts with organic acids come into consideration. Hydrochlorides, hydrobromides, sulphates, nitrates, citrates, acetates, maleates, succinates, methan-sulphonates, p-toluenesulphonates and the like are examples of such salts.

The following schemes 1–8 describe the processes for preparation of compounds of formula I in more detail. The starting materials are known compounds or can be prepared according to methods known in the art.

In the schemes the following abbreviations have been used:
dppf [1,1'-bis(diphenylphosphino)ferrocene]
DMF N,N-dimethylformamide
DMAP 4-(N,N-dimethylamino)pyridine
DPPA diphenylphosphoryl azide
THF tetrahydrofuran
PivCl pivaloyl chloride
THF tetrahydrofuran
TMEDA N,N,N',N'-tetramethylethylene diamine
DIPEA N-ethyldiisopropyl-amine
KHMDS potassium hexamethyldisilazide

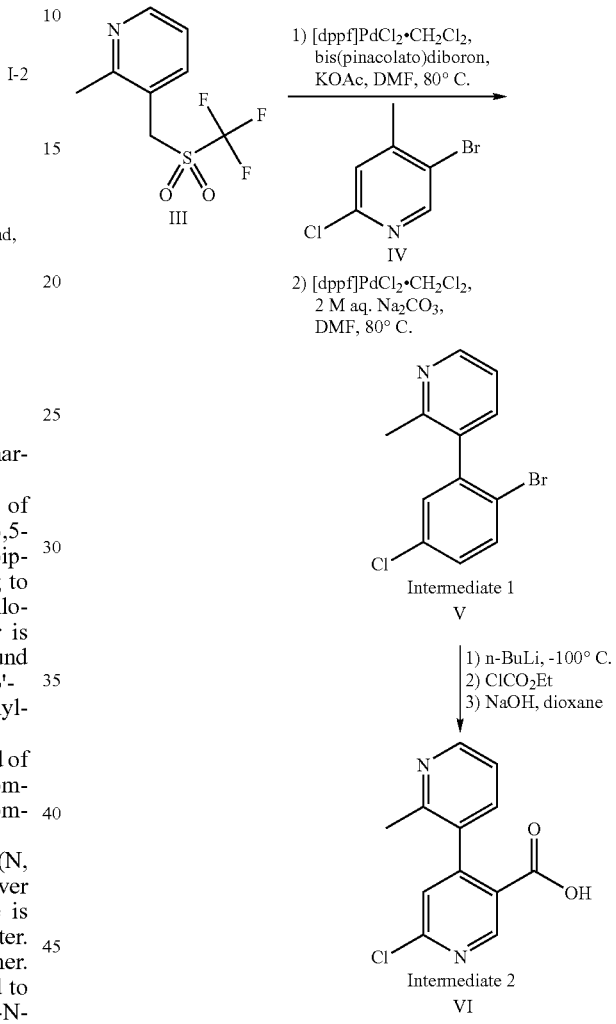

The intermediate 1 of formula V (5'-bromo-2'-chloro-2-methyl-[3,4']bipyridinyl) can be prepared as follows:

A mixture of trifluoro-methanesulfonic acid 2-methyl-pyridin-3-yl ester, bis(pinacolato)diboron, potassium acetate and dichloro[1,1'-bis(diphenylphosphino)ferrocene]palladium(II) dichloromethane adduct in N,N-dimethylformamide is heated at about 80° C. over night under argon. After cooling to room temperature 5-bromo-2-chloro-4-iodo-pyridine, another portion of dichloro[1,1'-bis(diphenylphosphino)ferrocene]palladium(II) dichloromethane adduct and a deoxygenated aqueous solution of sodium carbonate are added. The reaction mixture is heated at about 80° C. for 4.5 h. After cooling to room temperature the mixture is concentrated, dried and purified in conventional manner.

The intermediate 2 of formula VI (6'-chloro-2-methyl-[3,4']bipyridinyl-3'-carboxylic acid) can be prepared in the following way:

To a solution of 5'-bromo-2'-chloro-2-methyl-[3,4']bipyridinyl in tetrahydrofuran is added dropwise at about −100°

C. under argon a solution of n-butyllithium in hexane. After complete consumption of starting material, carbon dioxide gas is slowly bubbled through the reaction mixture. After approximately 15 min, the mixture is allowed to slowly warm to 0° C. and stirred at this temperature for about 1 h. Dilution with water is followed by basification to pH 9 by the addition of aqueous sodium hydroxide solution. After washing with tert-butyl methyl ether the aqueous layer is acidified to pH 3 by the addition of aqueous hydrochloric acid solution, concentrated, dried and purified in conventional manner.

Scheme 2

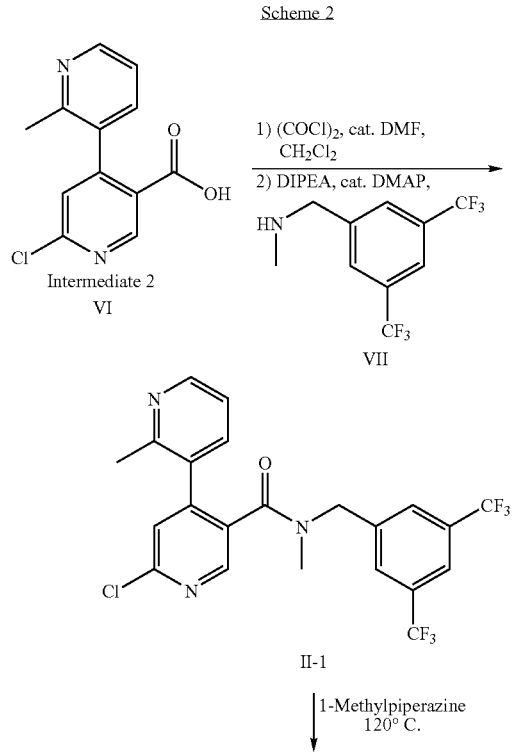

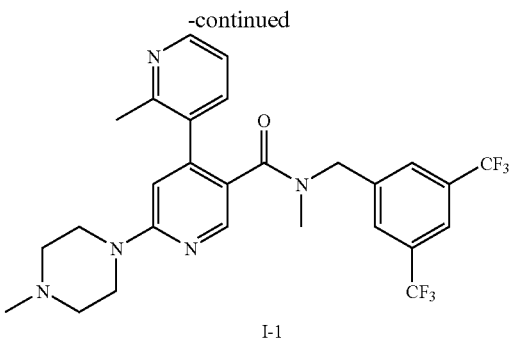

In accordance with scheme 2,2-methyl-6'-(4-methyl-piperazin-1-yl)-[3,4']bipyridinyl-3'-carboxylic acid (3,5-bis-trifluoromethyl-benzyl)-methyl-amide can be prepared as follows: To a suspension of 6'-chloro-2-methyl-[3,4']bipyridinyl-3'-carboxylic acid (VI) in dichloromethane are added, at about 0° C. under argon, oxalyl chloride and one drop of DMF. The reaction mixture is allowed to slowly warm to room temperature. After about 1 h the mixture is concentrated in vacuo and re-dissolved in dichloromethane. This solution is added dropwise at 0° C. to a mixture of (3,5-bis-trifluoromethyl-benzyl)-methyl-amine and N,N-diisopropylethylamine in dichloromethane. After about 30 min the reaction mixture is diluted with ethyl acetate and washed with an aqueous sodium hydroxide solution to give 6'-chloro-2-methyl-[3,4']bipyridinyl-3'-carboxylic acid (3,5-bis-trifluoromethyl-benzyl)-methyl-amide of formula II-1.

2-Methyl-6'-(4-methyl-piperazin-1-yl)-[3,4']bipyridinyl-3'-carboxylic acid (3,5-bis-trifluoromethyl-benzyl)-methyl-amide of formula I-1 is prepared as follows: A mixture of 6'-chloro-2-methyl-[3,4']bipyridinyl-3'-carboxylic acid (3,5-bis-trifluoromethyl-benzyl)-methyl-amide and 1-methylpiperazine is heated at about 120° C. for 2 h. After cooling to room temperature the mixture is diluted with dichloromethane and washed with water. The aqueous layer is worked up in conventional manner to give the compound 2-methyl-6'-(4-methyl-piperazin-1-yl)-[3,4']bipyridinyl-3'-carboxylic acid (3,5-bis-trifluoromethyl-benzyl)-methyl-amide of formula I-1.

Scheme 3

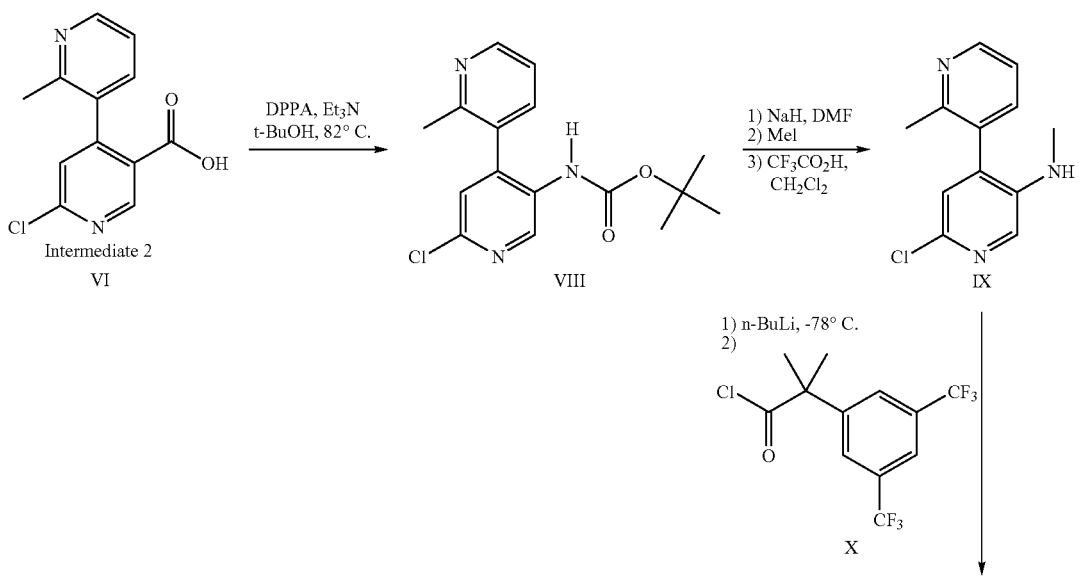

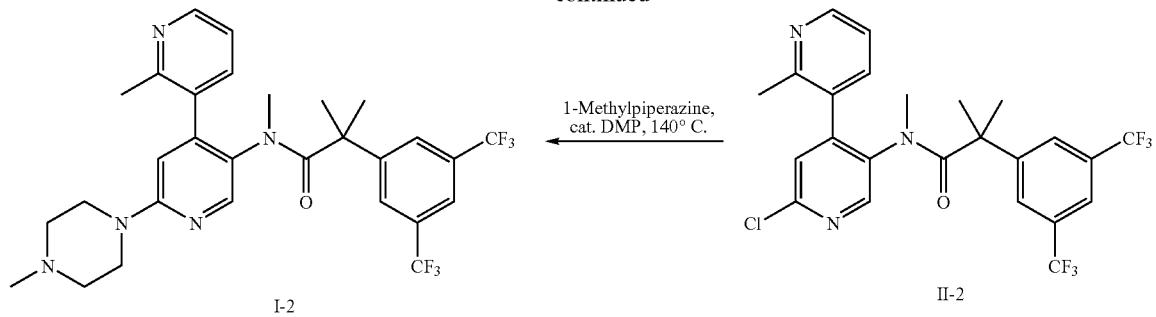

2-(3,5-Bis-trifluoromethyl-phenyl)-N-methyl-N-[2-methyl-6'-(4-methyl-piperazin-1-yl)-[3,4']bipyridinyl-3'-yl]-isobutyramide of formula I-2 can be prepared as follows: A solution of 6'-chloro-2-methyl-[3,4']bipyridinyl-3'-carboxylic acid (VI), triethylamine and diphenylphosphoryl azide in tert-butanol is stirred at about 90° C. under argon for 1.5 h. After cooling to room temperature, the solvent is evaporated. The residue is diluted with ethyl acetate and washed with aqueous sodium hydrogencarbonate solution and brine. The organic layer is concentrated and purified to give the compound (6'-chloro-2-methyl-[3,4']bipyridinyl-3'-yl)-carbamic acid tert-butyl ester of formula VIII.

To a solution of (6'-chloro-2-methyl-[3,4']bipyridinyl-3'-yl)-carbamic acid tert-butyl ester in DMF is added sodium hydride under nitrogen at room temperature. After stirring for 30 min methyl iodide is added. The reaction mixture is stirred for 1 h and quenched with water, followed by extraction with dichloromethane. The combined organic layers are concentrated and purified in conventional manner.

To a solution of the obtained (6'-chloro-2-methyl-[3,4']bipyridinyl-3'-yl)-methyl-carbamic acid tert-butyl ester in dichloromethane is added 0.40 ml trifluoroacetic acid at room temperature. The reaction mixture is stirred at this temperature for about 1.5 h. After addition of an aqueous sodium hydroxide solution, the mixture is extracted with dichloromethane. The combined organic layers are dried and concentrated to give the compound (6'-chloro-2-methyl-[3,4']bipyridinyl-3'-yl)-methyl-amine of formula IX.

To a solution of (6'-chloro-2-methyl-[3,4']bipyridinyl-3'-yl)-methyl-amine in THF is added a solution of n-butyllithium in hexanes at about −78° C. After 15 min 2-(3,5-bis-trifluoromethyl-phenyl)-2-methyl-propionyl chloride is added. The reaction mixture is allowed to warm to room temperature during 30 min. After addition of an aqueous sodium hydroxide solution, the mixture is extracted with dichloromethane, dried and concentrated to give the compound 2-(3,5-Bis-trifluoromethyl-phenyl)-N-(6'-chloro-2-methyl-[3,4']bipyridinyl-3'-yl)-N-methyl-isobutyramide of formula II-2.

A mixture of 2-(3,5-bis-trifluoromethyl-phenyl)-N-(6'-chloro-2-methyl-[3,4']bipyridinyl-3'-yl)-N-methyl-isobutyramide, 1-methylpiperazine and 4-(N,N-dimethylamino)pyridine is heated at about 140° C. over night. After cooling to room temperature the mixture is diluted with tert-butyl methyl ether and washed with water. The aqueous layer is extracted with tert-butyl methyl ether. The combined organic layers are dried and concentrated to give the compound 2-(3,5-Bis-trifluoromethyl-phenyl)-N-methyl-N-[2-methyl-6'-(4-methyl-piperazin-1-yl)-[3,4']bipyridinyl-3'-yl]-isobutyramide of formula I-2.

Alternatively, compounds of formula I can be prepared as described in EP 1035 115 A1 as shown in schemes 4 to 8:

Scheme 4

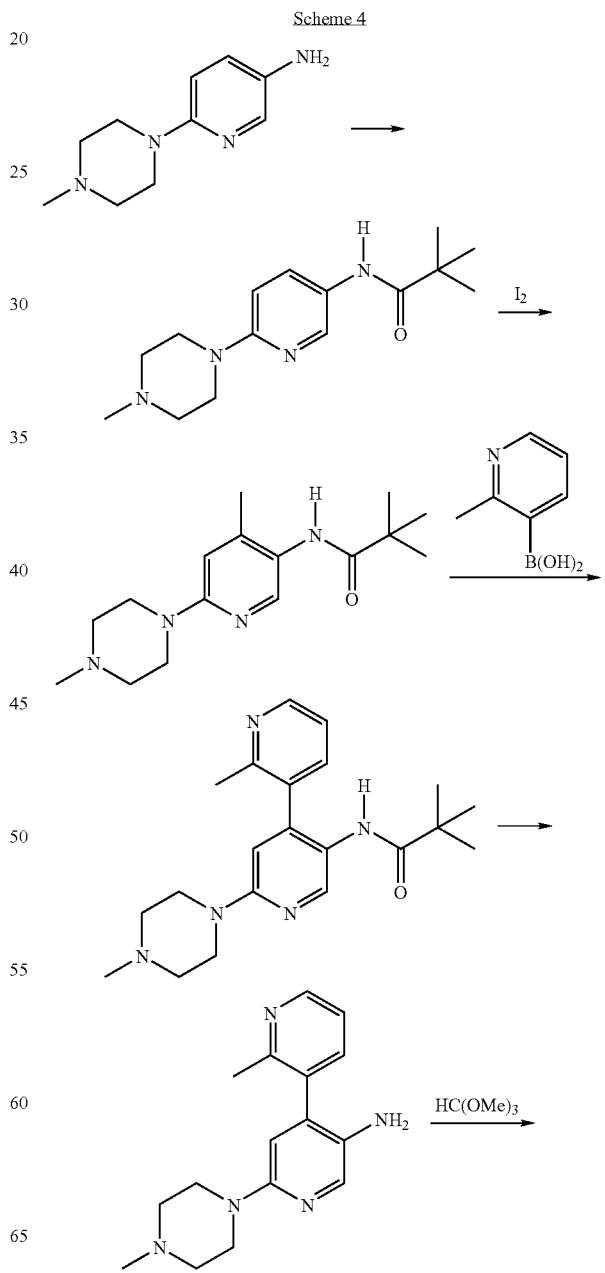

-continued
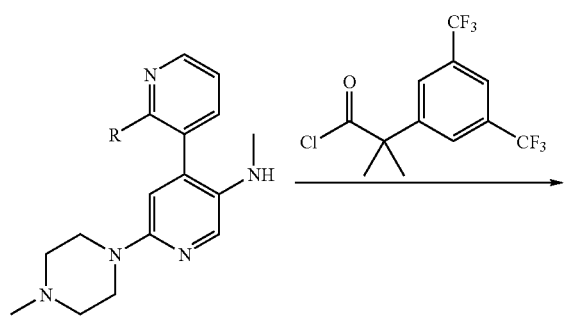
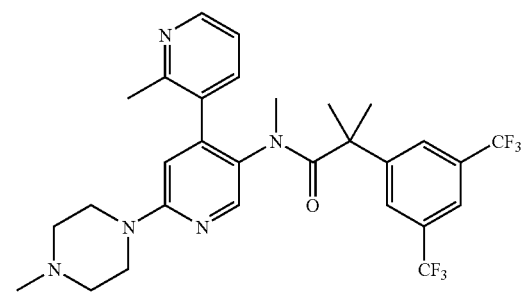
I-2
Scheme 5
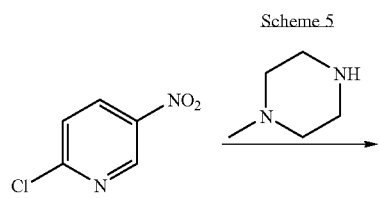
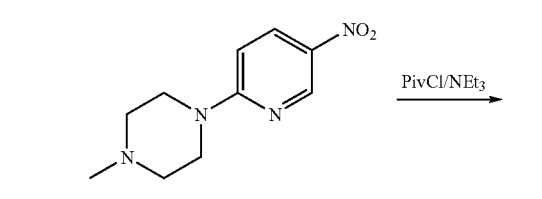
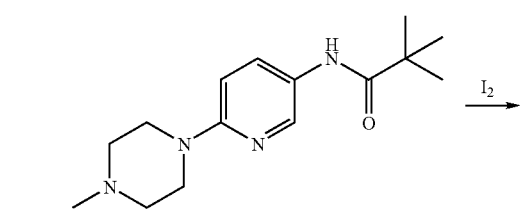
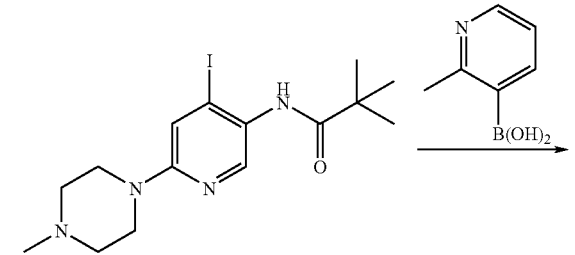
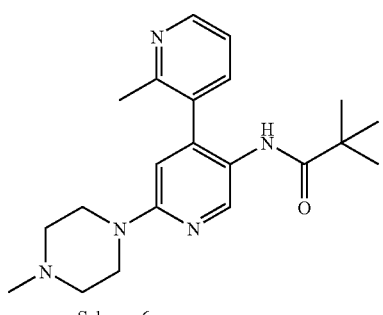
Scheme 6
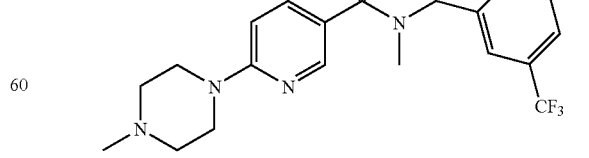
I-1
Z = Cl, Br, I or OS(O)₂C₆H₄CH₃

Scheme 7

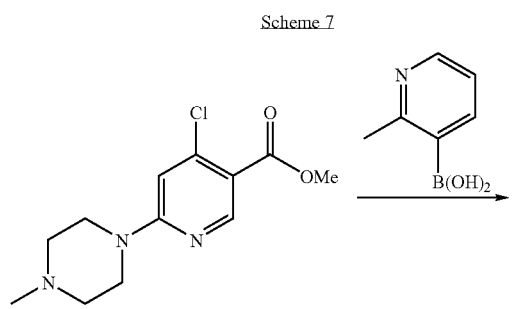

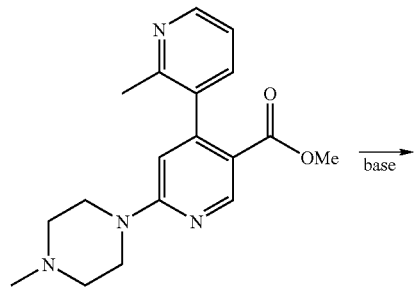

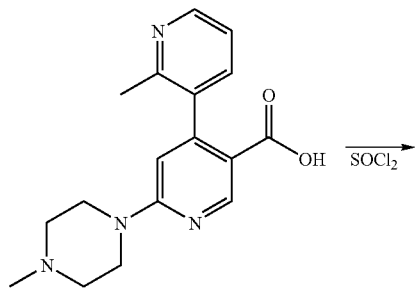

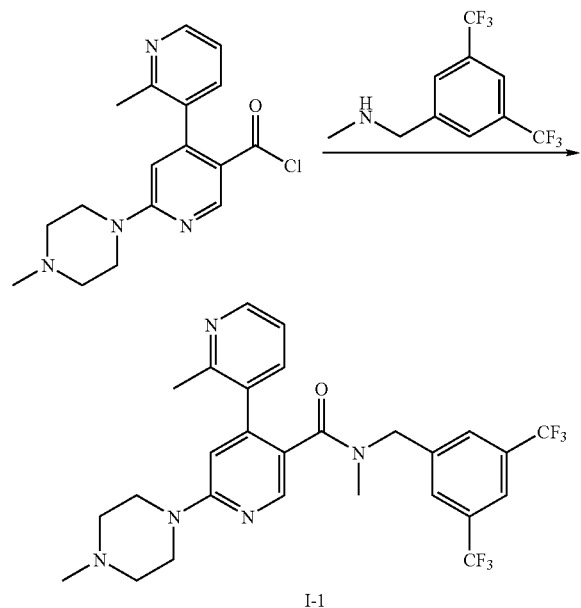

-continued
Scheme 8

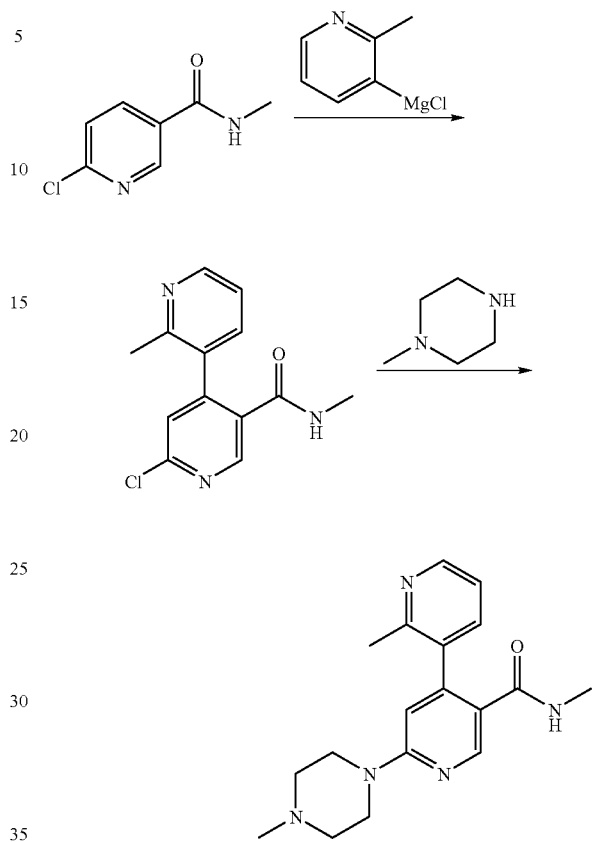

As mentioned earlier, the compounds of formula I and their pharmaceutically usable addition salts possess valuable pharmacological properties. It has been found that the compounds of the present invention are antagonists of the Neurokinin 1 (NK-1, substance P) receptor with a good solubility.

The compounds were investigated in accordance with the tests given hereinafter.

NK-1 Receptor Activity:

The affinity of test compounds for the NK-1 receptor was evaluated at human NK-1 receptors in CHO cells infected with the human NK-1 receptor (using the Semliki virus expression system) and radiolabelled with [$^3$H]substance P (final concentration 0.6 nM). Binding assays were performed in HEPES buffer (50 mM, pH 7.4) containing BSA (0.04%) leupeptin (8 μg/ml), MnCl$_2$ (3 mM) and phosphoramidon (2 μM). Binding assays consisted of 250 μl of membrane suspension (1.25×10$^5$ cells/assay tube), 0.125 μl of buffer of displacing agent and 125 μl of [$^3$H]substance P. Displacement curves were determined with at least seven concentrations of the compound. The assay tubes were incubated for 60 min at room temperature after which time the tube contents were rapidly filtered under vacuum through GF/C filters presoaked for 60 min with PEI (0.3%) with 2×2 ml washes of HEPES buffer (50 mM, pH 7.4). The radioactivity retained on the filters was measured by scintillation counting. All assays were performed in triplicate in at least 2 separate experiments.

Solubility

Method Description Equilibrium Solubility

Equilibrium solubility values were determined at pH 4.2 (0.15 M Citrat-buffer). A known amount of drug, generally 1–2 mg, was added to 250 µl of buffer (glass tubes) and the resulting suspension was stirred for 2 h (21° C.), after 5 minutes of sonification. The pH of the solution was checked and corrected if necessary (in case of pH correction, the solution was once more shaken and equilibrated) and after 24 h the suspension was filtered through a 0.65-µm filter. The filtered solution was then assayed by HPLC to determine the drug concentration. In cases where the drug had completely dissolved in the buffer, the value for equilibrium solubility was assumed to be higher than the value determined by HPLC and was reported as such. Stock solutions (~1 mg/ml) in DMSO were used in the preparation of a calibration curve in the related buffer using HPLC analytics.

Results

| —X—C(R¹)(R¹')— | Y | pK$_i$(NK-1) | Solubility (µg/mL, pH 4.2) | Example |
|---|---|---|---|---|
| N-C(=O) | CH | 9.01 | 26 | EP 1 035 115 A1 example 14 |
| N-C(=O) | N | 8.96 | 7500 | 2 |
| C(=O)-N | CH | 9.24 | 495 | EP 1 035 115 A1 example 12 |
| C(=O)-N | N | 8.56 | 13700 | 1 |

As shown by representative compounds in the table above that the compounds of the present invention possess a high affinity toward the NK-1 receptor and a very good water-solubility compared with structure-related compounds disclosed in the prior art.

The present invention also provides pharmaceutical compositions containing compounds of the invention, for example compounds of formula I and their pharmaceutically acceptable acid addition salts, and a pharmaceutically acceptable carrier. Such pharmaceutical compositions can be in the form of tablets, coated tablets, dragees, hard and soft gelatine capsules, solutions, emulsions or suspensions. The pharmaceutical compositions also can be in the form of suppositories or injectable solutions.

The pharmaceutical compounds of the invention, in addition to one or more compounds of the invention, contain a pharmaceutically acceptable carrier. Suitable pharmaceutically acceptable carriers include pharmaceutically inert, inorganic and organic carriers. Lactose, corn starch or derivatives thereof, talc, stearic acids or its salts and the like can be used, for example, as such carriers for tablets, coated tablets, dragees and hard gelatine capsules. Suitable carriers for soft gelatine capsules are, for example, vegetable oils, waxes, fats, semi-solid and liquid polyols and the like. Depending on the nature of the active substance no carriers are, however, usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

Moreover, the pharmaceutical compositions can contain preservatives, solubilizers, stabilizers, wetting agents, emulsifiers, sweeteners, colorants, flavorants, salts for varying the osmotic pressure, buffers, masking agents or antioxidants. They can also contain still other therapeutically valuable substances.

The present invention also provides a process for the manufacture of pharmaceutical compositions. Such process comprises bringing the compound of formula I and/or pharmaceutically acceptable acid addition salt thereof and, fir desired, one or more other therapeutically valuable substances into a galenical administration form together with one or more therapeutically inert carriers.

Compounds of the invention are NK-1 receptor antagonists. The present invention provides methods for the treatment of numerous inflammatory conditions, migraine, rheumatoid arthritis, asthma, inflammatory bowel disease, mediation of the emetic reflex, Parkinson's disease, anxiety, depression, pain, headache, migraine, Alzheimer's disease, multiple sclerosis, attenuation of morphine withdrawal, cardiovascular changes, oedema, such as oedema caused by thermal injury, chronic inflammatory diseases such as rheumatoid arthritis, asthma/bronchial hyperreactivity and other respiratory diseases including allergic rhinitis, inflammatory diseases of the gut including ulcerative colitis and Crohn's disease, ocular injury and ocular inflammatory diseases, traumatic brain injury, motion sickness, induced vomiting and psychoimmunologic and psychosomatic disorders.

Preferred indications in accordance with the present invention are disorders of the central nervous system. Thus, the invention provides a method for the treatment of depressive disorders which comprises administering to an individual a therapeutically effective amount of a compound of the invention. A major depressive episode has been defined as being a period of at least two weeks during which, for most of the day and nearly every day, there is either depressed mood or the loss of interest or pleasure in all, or nearly all activities. In another aspect, the invention provides a method for the treatment of emesis which comprises administering to an individual a therapeutically effective amount of a compound of the invention.

The dosage at which compounds of the invention can be administered can vary within wide limits and will, of course, be fitted to the individual requirements in each particular case. In general, in the case of oral administration a daily dosage of about 1 to 1000 mg per person of a compound of general formula I should be appropriate, although the above upper limit can also be exceeded when necessary.

The following Examples illustrate the present invention without limiting it. All temperatures are given in degrees Celsius.

Intermediate 1

5'-Bromo-2'-chloro-2-methyl-[3,4']bipyridinyl

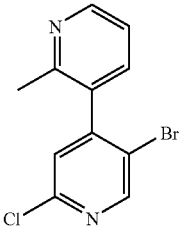

A mixture of 2.73 g (11.3 mmol) trifluoro-methanesulfonic acid 2-methyl-pyridin-3-yl ester, 3.16 g (12.4 mmol) bis(pinacolato)diboron, 3.33 g (33.9 mmol) potassium acetate and 0.46 g (0.56 mmol) dichloro[1,1'-bis(diphenylphosphino)ferrocene]palladium(II) dichloromethane adduct in 75 ml N,N-dimethylformamide was heated at 80° C. over night under argon. After cooling to room temperature 5.40 g (17.0 mmol) 5-bromo-2-chloro-4-iodo-pyridine, another portion of 0.46 g (0.56 mmol) dichloro[1,1'-bis(diphenylphosphino)ferrocene]palladium (II) dichloromethane adduct and 30 ml of a deoxygenated 2 M aqueous solution of sodium carbonate were added. The reaction mixture was heated at 80° C. for 4.5 h. After cooling to room temperature the mixture was diluted with water and extracted with three portions of tert-butyl methyl ether. The combined organic layers were dried over sodium sulfate and concentrated in vacuo. Flash column chromatography gave 1.00 (31%) of the title compound as a light yellow solid.

MS m/e (%): 285 (M+H$^+$, 100)

Intermediate 2

6'-Chloro-2-methyl-[3,4']bipyridinyl-3'-carboxylic acid

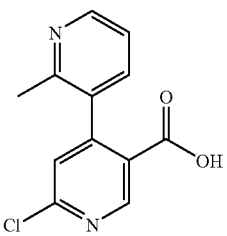

To a solution of 1.24 g (4.36 mmol) 5'-bromo-2'-chloro-2-methyl-[3,4']bipyridinyl in ml tetrahydrofuran were added dropwise at −100° C. under argon 3.0 ml (4.8 mmol) of a 1.6 M solution of n-butyllithium in hexanes. After complete consumption of starting material carbon dioxide gas was slowly bubbled through the reaction mixture. After approximately 15 min. the mixture was allowed to slowly warm to 0° C. and stirred at this temperature for 1 h. Dilution with water was followed by basification to pH 9 by the addition of 1 M aqueous sodium hydroxide solution. After washing with three portions of tert-butyl methyl ether the aqueous layer was acidified to pH 3 by the addition of 1 M aqeous hydrochloric acid solution and extracted with dichloromethane. The combined organic layers were dried over sodium sulfate and concentrated in vacuo to give 0.52 g (48%) of the crude title compound as a light red solid.

MS m/e (%): 247 (M−H$^+$, 100)

EXAMPLE 1

2-Methyl-6'-(4-methyl-piperazin-1-yl)-[3,4']bipyridinyl-3'-carboxylic acid (3,5-bis-trifluoromethyl-benzyl)-methyl-amide a) 6'-Chloro-2-methyl-[3,4']bipyridinyl-3'-carboxylic acid (3,5-bis-trifluoromethyl-benzyl)-methyl-amide

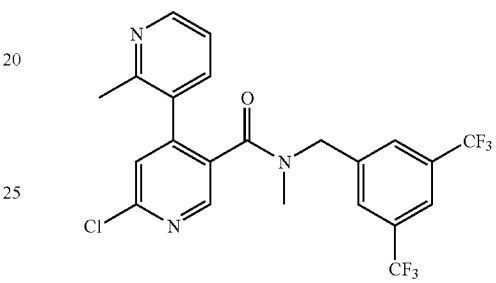

To a suspension of 0.10 g (0.40 mmol) 6'-chloro-2-methyl-[3,4']bipyridinyl-3'-carboxylic acid in 4 ml dicloromethane were added dropwise at 0° C. under argon 0.05 ml (0.6 mmol) oxalyl chloride and one drop of DMF. The reaction mixture was allowed to slowly warm to room temperature. After 1 h the mixture was concentrated in vacuo and redissolved in 2 ml dichloromethane. This solution was added dropwise at 0° C. to a mixture of 0.16 g (0.60 mmol) (3,5-bis-trifluoromethyl-benzyl)-methyl-amine and 0.14 ml (0.80 mmol) N,N-diisopropylethylamine in 2 ml dichloromethane. After 30 min. the reaction mixture was diluted with ethyl acetate and washed with a 1 M aqueous sodium hydroxide solution. The aqueous layer was extracted with ethyl acetate. The combined organic layers were dried over sodium sulfate and concentrated in vacuo to give 0.29 g of crude product. Flash chromatography gave 0.21 g (quant.) of the title compound.

MS m/e (%): 488 (M+H$^+$, 100)

b) 2-Methyl-6'-(4-methyl-piperazin-1-yl)-[3,4']bipyridinyl-3'-carboxylic acid (3,5-bis-trifluoromethyl-benzyl)-methyl-amide

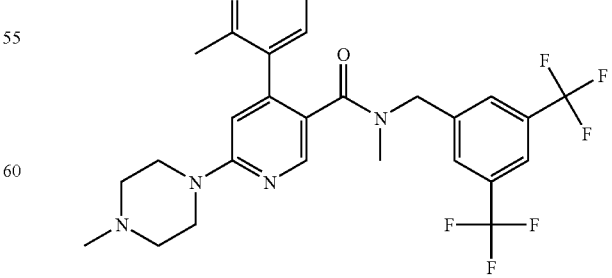

A mixture of 0.21 g (0.44 mmol) 6'-chloro-2-methyl-[3,4']bipyridinyl-3'-carboxylic acid (3,5-bis-trifluoromethylbenzyl)-methyl-amide and 1.0 ml (9.0 mmol) 1-methylpiperazine was heated at 120° C. for 2 h. After cooling to room temperature the mixture was diluted with dichloromethane and washed with water. The aqueous layer was extracted with dichloromethane. The combined organic layers were dried over sodium sulfate and concentrated in vacuo to give 0.25 g of crude product. Flash chromatography gave 0.17 g (70%) of the title compound. MS m/e (%): 552 (M+H$^+$, 100)

EXAMPLE 2

2-(3,5-Bis-trifluoromethyl-phenyl)-N-methyl-N-[2-methyl-6'-(4-methyl-piperazin-1-yl)-[3,4']bipyridinyl-3'-yl]-isobutyramide a) (6'-Chloro-2-methyl-[3,4']bipyridinyl-3'-yl)-carbamic acid tert-butyl ester

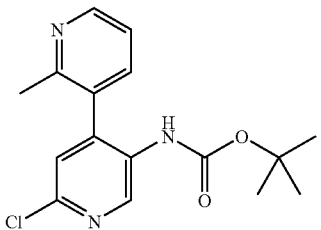

A solution of 0.20 g (0.80 mmol) 6'-chloro-2-methyl-[3,4']bipyridinyl-3'-carboxylic 0.23 ml (1.6 mmol) triethylamine and 0.18 ml (0.80 mmol) diphenylphosphoryl azide in 12 ml tert-butanol was stirred at 90° C. under argon for 1.5 h. After cooling to room temperature the solvent was evaporated. The residue was diluted with ethyl acetate and washed with aqueous sodium hydrogencarbonate solution and brine. The organic layer was dried over sodium sulfate and concentrated. Flash chromatography gave 0.13 g (48%) of the title compound.

MS m/e (%): 320 (M+H$^+$, 100)

b) (6'-Chloro-2-methyl-[3,4']bipyridinyl-3'-yl)-methyl-carbamic acid tert-butyl ester

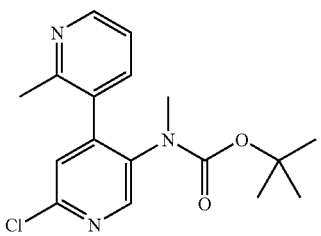

To a solution of 0.16 g (0.50 mmol) (6'-chloro-2-methyl-[3,4']bipyridinyl-3'-yl)-carbamic acid tert-butyl ester in 5 ml DMF were added 25 mg (0.50 mmol) sodium hydride (50% suspension in mineral oil) under nitrogen at room temperature. After stirring for 30 min 0.034 ml (0.52 mmol) methyl iodide were added. The reaction mixture was stirred for 1 h. Quenching with water was followed by extraction with three portions of dichloromethane. The combined organic layers were washed with water. The combined aqueous layers were extracted with dichloromethane. The combined organic layers were dried with sodium sulfate and concentrated. Residual DMF was removed by Kugelrohr distillation. Flash chromatography gave 0.14 g (84%) of the title compound.

MS m/e (%): 334 (M+H$^+$, 100)

c) (6'-Chloro-2-methyl-[3,4']bipyridinyl-3'-yl)-methyl-amine

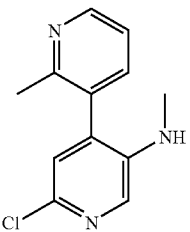

To a solution of 0.14 g (0.42 mmol) (6'-chloro-2-methyl-[3,4']bipyridinyl-3'-yl)-methyl-carbamic acid tert-butyl ester in 1.2 ml dichloromethane were added 0.40 ml (5.2 mmol) trifluoroacetic acid at room temperature. The reaction mixture was stirred at this temperature for 1.5 h. After addition of a 2 M aqueous sodium hydroxide solution the mixture was extracted with three portions of dichloromethane. The combined organic layers were dried over sodium sulfate and concentrated. Flash chromatography gave 66 mg (68%) of the title compound.

MS m/e (%): 234 (M+H$^+$, 100)

d) 2-(3,5-Bis-trifluoromethyl-phenyl)-N-(6'-chloro-2-methyl-[3,4']bipyridinyl-3'-yl)-N-methyl-isobutyramide

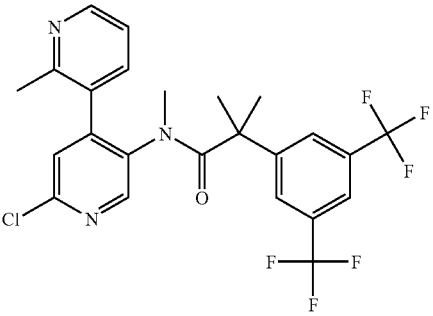

To a solution of 0.19 g (0.81 mmol) (6'-chloro-2-methyl-[3,4']bipyridinyl-3'-yl)-methyl-amine in 8 ml THF were added 0.52 ml (0.83 mmol) of a 1.6 M solution of n-butyllithium in hexanes at −78° C. After 15 min 0.28 g (0.88 mmol) 2-(3,5-bis-trifluoromethyl-phenyl)-2-methyl-propionyl chloride were added. The reaction mixture was allowed to warm to room temperature during 30 min. After addition of a 0.2 M aqueous sodium hydroxide solution the mixture was extracted with three portions of dichloromethane. The combined organic layers were dried over sodium sulfate and concentrated. Flash chromatography gave 0.30 g (73%) of the title compound.

MS m/e (%): 516 (M+H$^+$, 100)

e) 2-(3,5-Bis-trifluoromethyl-phenyl)-N-methyl-N-[2-methyl-6'-(4-methyl-piperazin-1-yl)-[3,4']bipyridinyl-3'-yl]-isobutyramide

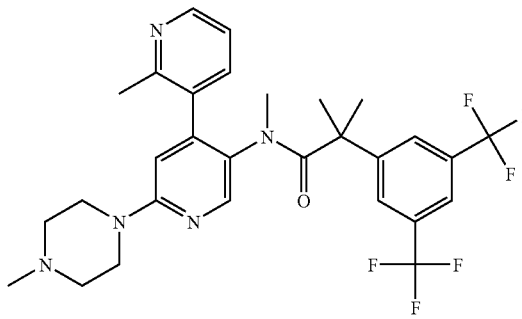

A mixture of 0.16 g (0.30 mmol) 2-(3,5-bis-trifluoromethyl-phenyl)-N-(6'-chloro-2-methyl-[3,4']bipyridinyl-3'-yl)-N-methyl-isobutyramide, 0.67 ml (6.0 mmol) 1-methylpiperazine and 2 mg (0.02 mmol) 4-(N,N-dimethylamino) pyridine was heated at 140° C. over night. After cooling to room temperature the mixture was diluted with tert-butyl methyl ether and washed with water. The aqueous layer was extracted with two portions of tert-butyl methyl ether. The combined organic layers were dried over sodium sulfate and concentrated in vacuo. Flash chromatography gave 0.16 g (93%) of the title compound.

MS m/e (%): 580 (M+H$^+$, 100)

EXAMPLE A

Tablets of the following composition are manufactured in the usual manner:

|  | mg/tablet |
| --- | --- |
| Active substance | 5 |
| Lactose | 45 |
| Corn starch | 15 |
| Microcrystalline cellulose | 34 |
| Magnesium stearate | 1 |
| Tablet weight | 100 |

EXAMPLE B

Capsules of the following composition are manufactured:

|  | mg/capsule |
| --- | --- |
| Active substance | 10 |
| Lactose | 155 |
| Corn starch | 30 |
| Talc | 5 |
| Capsule fill weight | 200 |

The active substance, lactose and corn starch are firstly mixed in a mixer and then in a comminuting machine. The mixture is returned to the mixer, the talc is added thereto and mixed thoroughly. The mixture is filled by machine into hard gelatine capsules.

EXAMPLE C

Suppositories of the following composition are manufactured:

|  | mg/supp. |
| --- | --- |
| Active substance | 15 |
| Suppository mass | 1285 |
| Total | 1300 |

The suppository mass is melted in a glass or steel vessel, mixed thoroughly and cooled to 45° C. Thereupon, the finely powdered active substance is added thereto and stirred until it has dispersed completely. The mixture is poured into suppository moulds of suitable size, left to cool, the suppositories are then removed from the moulds and packed individually in wax paper or metal foil.

The invention claimed is:
1. A compound of formula I

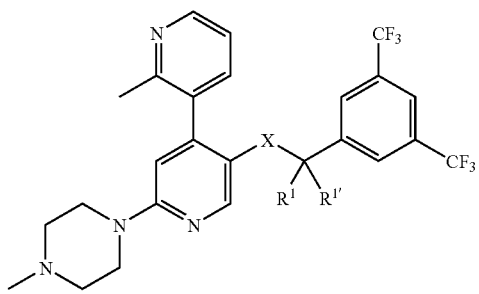

wherein
R$^1$ and R$^{1'}$ are each independently hydrogen or methyl;
X is —C(O)N(CH$_3$)— or —N(CH$_3$)C(O)—;
or a pharmaceutically acceptable acid addition salt thereof.
2. The compound of claim 1, which is 2-methyl-6'-(4-methyl-piperazin-1-yl)-[3,4']bipyridinyl-3'-carboxylic acid (3,5-bis-trifluoromethyl-benzyl)-methyl-amide.
3. The compound of claim 1, which is 2-(3,5-bis-trifluoromethyl-phenyl)-N-methyl-N-[2-methyl-6'-(4-methyl-piperazin-1-yl)-[3,4']bipyridinyl-3'-yl]-isobutyramide.
4. A pharmaceutical composition comprising a therapeutically effective amount of a compound of formula I

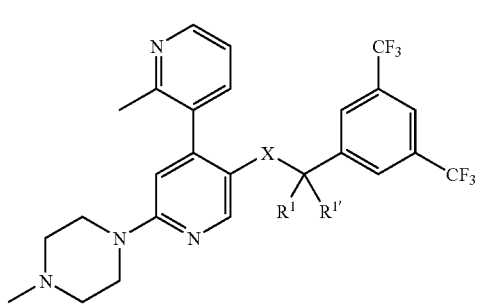

wherein
R¹ and R¹' are each independtly hydrogen or methyl;
X is —C(O)N(CH₃)— or —N(CH₃)C(O)—;
or a pharmaceutically acceptable acid addition salt thereof and a pharmaceutically acceptable carrier.

5. The composition of claim 4, wherein the compound of formula I is
2-methyl-6'-(4-methyl-piperazin-1-yl)-[3,4']bipyridinyl-3'-carboxylic acid (3,5-bis-trifluoromethyl-benzyl)-methyl-amide.

6. The composition of claim 4, wherein the compound of formula I is
2-(3,5-bis-trifluoromethyl-phenyl)-N-methyl-N-[2-methyl-6'-(4-methyl-piperazin-1-yl)-[3,4']bipyridinyl-3'-yl]-isobutyramide.

7. A process for preparing a compound of formula I

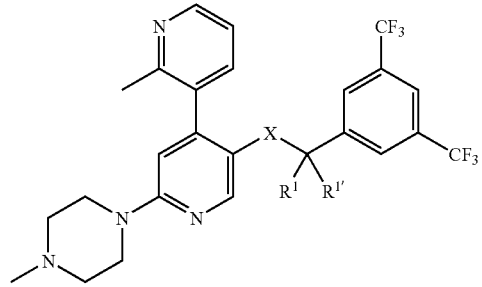

I wherein
R¹ and R¹' are each independtly hydrogen or methyl;
X is —C(O)N(CH₃)— or —N(CH₃)C(O)—;
selected from the group consisting of
a) reacting a compound of formula

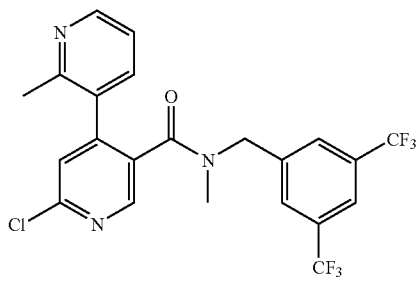

II-1 with 1-methyl-piperazine of formula

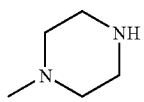

to give a compound of formula

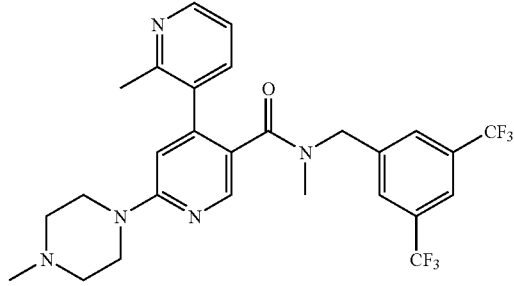

I-1 and
b) reacting a compound of formula

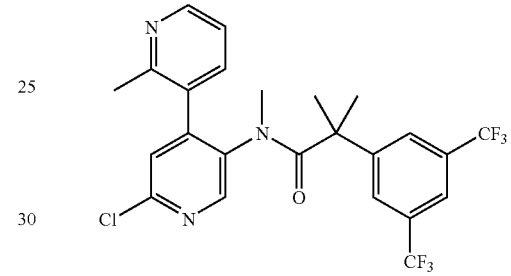

II-2 with 1-methyl-piperazine of formula

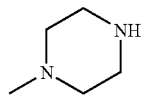

to give a compound of formula

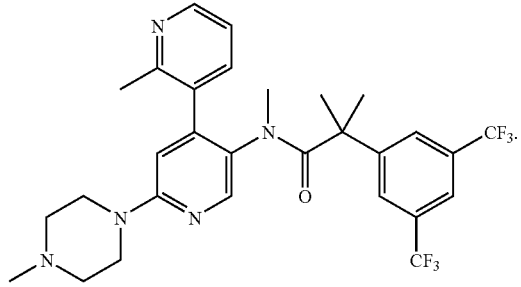

I-2

* * * * *